(12) United States Patent
Axelson, Jr. et al.

(10) Patent No.: US 7,618,421 B2
(45) Date of Patent: Nov. 17, 2009

(54) TOOLS FOR FEMORAL RESECTION IN KNEE SURGERY

(75) Inventors: Stuart L. Axelson, Jr., Succasunna, NJ (US); Gearoid Walsh, Co. Clare (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 896 days.

(21) Appl. No.: 09/974,524

(22) Filed: Oct. 10, 2001

(65) Prior Publication Data
US 2003/0069585 A1  Apr. 10, 2003

(51) Int. Cl.
*A61B 17/56* (2006.01)
(52) U.S. Cl. .......................................... 606/88
(58) Field of Classification Search ................... 606/88, 606/86, 87, 89, 96, 97, 98, 102
See application file for complete search history.

(56) References Cited

U.S. PATENT DOCUMENTS

| | | | |
|---|---|---|---|
| 2,697,433 A | 12/1954 | Zehnder | |
| 3,945,377 A | 3/1976 | Kronner | |
| 4,457,307 A | 7/1984 | Stillwell | |
| 4,474,177 A | 10/1984 | Whiteside | |
| 4,487,203 A | 12/1984 | Androphy | |
| 4,502,483 A | 3/1985 | Lacey | |
| 4,524,766 A | 6/1985 | Petersen | |
| 4,567,885 A | 2/1986 | Androphy | |
| 4,574,794 A | 3/1986 | Cooke et al. | |
| 4,646,729 A | 3/1987 | Kenna et al. | |
| 4,653,488 A | 3/1987 | Kenna | |
| 4,703,751 A | 11/1987 | Pohl | |
| 4,718,413 A | 1/1988 | Johnson | |
| 4,759,350 A | 7/1988 | Dunn et al. | |
| 4,841,975 A | 6/1989 | Woolson | |
| 4,892,093 A | 1/1990 | Zarnowski et al. | |
| 4,893,619 A | 1/1990 | Dale et al. | |
| 4,979,949 A | 12/1990 | Matsen, III et al. | |
| 5,002,547 A | 3/1991 | Poggie et al. | |
| 5,053,037 A | 10/1991 | Lackey | |
| 5,122,144 A | 6/1992 | Bert et al. | |
| 5,122,145 A * | 6/1992 | Fishbane ..................... 606/102 |
| 5,171,244 A | 12/1992 | Caspari et al. | |
| 5,282,803 A | 2/1994 | Lackey | |
| 5,342,368 A | 8/1994 | Petersen | |
| 5,364,402 A | 11/1994 | Mumme et al. | |

(Continued)

FOREIGN PATENT DOCUMENTS

EP   0 187 283   7/1986

(Continued)

*Primary Examiner*—Eduardo C Robert
*Assistant Examiner*—David Comstock
(74) *Attorney, Agent, or Firm*—Lerner, David, Littenberg, Krumholz & Mentlik, LLP

(57) ABSTRACT

Tools for resecting the femur include an anchoring device, a three-way alignment guide and a six way alignment guide attachable to the anchoring device, a resection guide attachable to the three-way alignment guide and equipped with couplings for trackers, an A-P sizer, a femoral sizing block bushing attachable to the six-way alignment guide, a 4-in-1 femoral cutting block, a 5-in-1 positional alignment guide attachable to the six-way alignment guide, a pair of diodes, and a 5-in-one cutting block. Methods of utilizing the apparatus are also disclosed.

15 Claims, 14 Drawing Sheets

U.S. PATENT DOCUMENTS

| | | | |
|---|---|---|---|
| 5,417,694 A | 5/1995 | Marik et al. | |
| 5,417,695 A | 5/1995 | Axelson, Jr. | |
| 5,445,642 A | 8/1995 | McNulty et al. | |
| 5,454,816 A * | 10/1995 | Ashby | 606/88 |
| 5,474,559 A * | 12/1995 | Bertin et al. | 606/89 |
| 5,486,178 A * | 1/1996 | Hodge | 606/82 |
| 5,514,139 A | 5/1996 | Goldstein et al. | |
| 5,562,675 A | 10/1996 | McNulty et al. | |
| 5,569,261 A | 10/1996 | Marik et al. | |
| 5,601,563 A | 2/1997 | Burke et al. | |
| 5,624,444 A | 4/1997 | Wixon et al. | |
| 5,643,272 A | 7/1997 | Haines et al. | |
| 5,653,714 A | 8/1997 | Dietz et al. | |
| 5,658,292 A | 8/1997 | Axelson, Jr. | |
| 5,676,668 A * | 10/1997 | McCue et al. | 606/87 |
| 5,681,316 A | 10/1997 | DeOrio et al. | |
| 5,688,279 A | 11/1997 | McNulty et al. | |
| 5,690,635 A | 11/1997 | Matsen, III et al. | |
| 5,704,941 A * | 1/1998 | Jacober et al. | 606/88 |
| 5,720,752 A | 2/1998 | Elliott et al. | |
| 5,743,915 A | 4/1998 | Bertin et al. | |
| 5,749,876 A | 5/1998 | Duvillier et al. | |
| 5,788,700 A * | 8/1998 | Morawa et al. | 606/88 |
| 5,810,827 A | 9/1998 | Haines et al. | |
| 5,817,097 A | 10/1998 | Howard et al. | |
| 5,830,216 A | 11/1998 | Insall et al. | |
| 5,855,582 A * | 1/1999 | Gildenberg | 606/130 |
| 5,997,543 A | 12/1999 | Truscott | |
| 6,013,081 A | 1/2000 | Burkinshaw et al. | |
| 6,024,746 A | 2/2000 | Katz | |
| 6,056,754 A | 5/2000 | Haines et al. | |
| 6,059,831 A | 5/2000 | Braslow et al. | |
| 6,063,091 A * | 5/2000 | Lombardo et al. | 606/88 |
| 6,077,270 A | 6/2000 | Katz | |
| 6,090,114 A * | 7/2000 | Matsuno et al. | 606/88 |
| 6,096,082 A | 8/2000 | Stegmuller et al. | |
| 6,173,200 B1 | 1/2001 | Cooke et al. | |
| 6,258,096 B1 | 7/2001 | Seki | |
| 6,267,762 B1 | 7/2001 | Millard et al. | |
| 6,285,902 B1 | 9/2001 | Kienzle, III et al. | |
| 6,348,058 B1 | 2/2002 | Melkent et al. | |
| 6,385,475 B1 | 5/2002 | Cinquin et al. | |
| 6,482,208 B1 * | 11/2002 | Ahrend et al. | 606/74 |
| 6,503,255 B1 | 1/2003 | Albrektsson et al. | |
| 6,514,259 B2 | 2/2003 | Picard et al. | |
| 6,551,325 B2 | 4/2003 | Neunauer et al. | |
| 6,554,837 B1 | 4/2003 | Hauri et al. | |
| 6,558,391 B2 * | 5/2003 | Axelson et al. | 606/88 |
| 6,685,711 B2 | 2/2004 | Axelson, Jr. et al. | |
| 6,695,848 B2 | 2/2004 | Haines | |
| 6,796,986 B2 * | 9/2004 | Duffner | 606/87 |
| 2001/0001121 A1 | 5/2001 | Lombardo et al. | |
| 2002/0133160 A1 | 9/2002 | Axelson, Jr. et al. | |
| 2002/0133161 A1 | 9/2002 | Axelson, Jr. et al. | |
| 2002/0133162 A1 | 9/2002 | Axelson, Jr. et al. | |

FOREIGN PATENT DOCUMENTS

| | | |
|---|---|---|
| EP | 0 322 363 B1 | 12/1988 |
| EP | 0 538 153 B1 | 4/1993 |
| EP | 0 551 572 B1 | 7/1993 |
| FR | 2644157 | 1/1992 |
| FR | 2 703 584 | 10/1994 |
| FR | 2776176 | 9/1999 |
| WO | WO-00 00093 | 1/2000 |

* cited by examiner

TOOLS FOR FEMORAL RESECTION IN KNEE SURGERY

This application is related to patent application Ser. No. 09/811,272, filed Mar. 17, 2001, entitled "Tools Used In Performing Femoral And Tibial Resection In Knee Surgery"; patent application Ser. No. 09/811,043, filed Mar. 17, 2001, entitled "Methods Used In Performing Femoral And Tibial Resection In Knee Surgery"; patent application Ser. No. 09/811,042, filed Mar. 17, 2001, entitled "Systems Used In Performing Femoral And Tibial Resection In Knee Surgery"; patent application Ser. No. 09/811,318, filed Mar. 17, 2001, entitled "Apparatus Used In Performing Femoral And Tibial Resection In Knee Surgery" and patent application Ser. No. 09/746,800 filed Dec. 23, 2000, entitled "Methods and Tools For Femoral Resection In Primary Knee Surgery", the complete disclosures of which are hereby incorporated by reference herein.

BACKGROUND OF THE INVENTION

1. Field of the Invention

The invention relates to methods and tools used in knee arthroplasty. More particularly, the invention relates to methods and tools used in knee surgery where artificial femoral and tibial components are installed.

2. Brief Description of the Prior Art

Total knee arthroplasty involves the replacement of portions of the patellar, femur and tibia with artificial components. In particular, a proximal portion of the tibia and a distal portion of the femur are cut away (resected) and replaced with artificial components.

As used herein, when referring to bones or other body parts, the term "proximal" means closest to the heart and the term "distal" means more distant from the heart. When referring to tools and instruments, the term "proximal" means closest to the practitioner and the term "distal" means distant from the practitioner.

There are several types of knee prostheses known in the art. One type is sometimes referred to as a "resurfacing type". In these prostheses, the articular surface of the distal femur and proximal tibia are "resurfaced" with respective metal and plastic condylar-type articular bearing components.

The femoral component is a metallic alloy construction (cobalt-chrome alloy or 6A14V titanium alloy) and provides medial and lateral condylar bearing surfaces of multi-radius design of similar shape and geometry as the natural distal femur or femoral-side of the knee joint.

One important aspect of these procedures is the correct resection of the distal femur and proximal tibia. These resections must provide planes which are correctly angled in order to properly accept the prosthetic components. In particular, the resection planes must be correctly located relative to three parameters: proximal-distal location, varus-valgus angle, and flexion-extension angle.

Moreover, following distal resection, the femur must be shaped with the aid of a cutting block. The cutting block must be correctly located relative to internal-external rotation, medial-lateral position, and anterior-posterior position.

Recently, various computerized systems have been introduced to aid the practitioner during different surgical procedures. A typical system is described in the attached Appendix.

These systems include multiple video cameras which are deployed above the surgical site and a plurality of dynamic reference frame (DRF) devices, also known as trackers, which are attached to body parts and surgical instruments. The trackers are generally LED devices which are visible to the cameras. Using software designed for a particular surgical procedure, a computer receiving input from the cameras guides the placement of surgical instruments.

The prior art instruments used for determining the correct planes for tibial and femoral resection in total knee arthroplasty are not well suited for use with computerized systems. The known tools utilize either intra-medullary alignment or extra-medullary alignment and adjustment of the degrees of freedom simultaneously is difficult or impossible. Moreover, in order to be useful with computer aided navigation systems, trackers must be attached to the tools. Existing tools do not permit the attachment of trackers.

SUMMARY OF THE INVENTION

It is therefore an object of the invention to provide methods and tools for performing femoral resection.

It is also an object of the invention to provide methods and tools for femoral resection which allow location of a cutting guide relative to six parameters.

It is another object of the invention to provide methods and tools for femoral resection which are infinitely adjustable.

It is still another object of the invention to provide methods and tools for femoral resection which are adapted to be used with computer aided navigation systems.

In accord with these objects which will be discussed in detail below, the tools according to a first embodiment of the present invention include an anchoring device for attachment to the femur and, a three-way alignment guide attachable to the anchoring device and adjustable relative to three parameters, a resection guide attachable to the alignment guide and equipped with couplings for trackers, an adjustable anterior-posterior sizer, a distal-proximal medial-lateral positioning guide, a medial-lateral cam lock, an anterior-posterior positioning guide, a femoral sizing block bushing, and femoral cutting guide.

The tools according to a second embodiment of the present invention include an anchoring device for attachment to the femur and, a six-way alignment guide attachable to the anchoring device and adjustable relative to six parameters, a pivotal 5-in-1 positional alignment jig attachable to the alignment guide and equipped with couplings for trackers, a pair of mounting diodes attachable to the epicondylar region of the femur, and a 5-in-1 cutting guide mountable on the diodes.

A first embodiment of the methods of the invention includes operating the computer aided navigation apparatus in the conventional manner including attaching one or more trackers to the bone to be resected; choosing a location for the anchoring device with or without guidance from the computer and installing the anchoring device; attaching the three-way alignment guide to the anchoring device; attaching a resection guide to the alignment guide; attaching one or two trackers to the resection guide; locating the resection guide with the aid of the alignment guide and the computer; fixing the resection guide to the bone with pins through the rotatable pin guides; and resecting the bone.

After the bone is resected, the adjustable anterior-posterior sizer is used to size the femur.

Next, the distal-proximal medial-lateral positioning guide, medial-lateral cam lock, anterior-posterior positioning guide, and femoral sizing block bushing are attached to the alignment guide.

The distal-proximal medial-lateral positioning guide, medial-lateral cam lock, and anterior-posterior positioning guide, when attached to the three-way guide, convert the three-way guide into a six-way guide. A tracker is preferably attached to the femoral sizing block bushing. The position of the bushing is adjusted in proximal-distal, varus-valgus, medial-lateral, and anterior-posterior directions. Two holes are drilled using the bushing as a guide. The femoral cutting guide is attached to the holes and the anterior and posterior cuts and chamfer cuts are made.

A second embodiment of the methods of the invention includes operating the computer aided navigation apparatus in the conventional manner including attaching one or more trackers to the bone to be resected; choosing a location for the anchoring device with or without guidance from the computer and installing the anchoring device; attaching the six-way alignment guide to the anchoring device; attaching the pivotal 5-in-1 positional alignment jig to the alignment guide; attaching a tracker to the jig; positioning the jig in the varus-valgus, flexion-extension, internal-external rotation, distal-proximal, and anterior-posterior directions; drilling four holes in the epicondylar region using the jig as a guide; removing the jig, the alignment guide, and the anchoring device; installing a pair of diodes in the epicondylar region with screws in the holes; and mounting the 5-in-1 cutting guide on the diodes.

The 5-in-1 cutting guide is then used to perform all of the femoral cuts as described in previously incorporated application Ser. No. 09/746,800.

BRIEF DESCRIPTION OF THE APPENDIX

The attached ten page Appendix describes the parts and assembly of a computer navigation system suitable for use with the invention.

DETAILED DESCRIPTION

Figure 1:
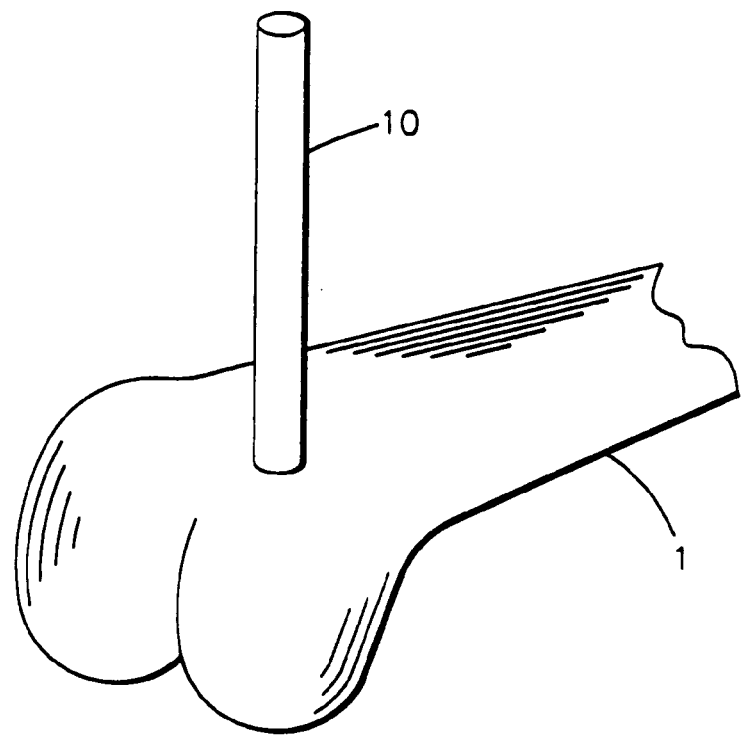
FIG. 1 is a broken perspective view of the distal femur with an anchoring device according to the invention.
Figure 2:
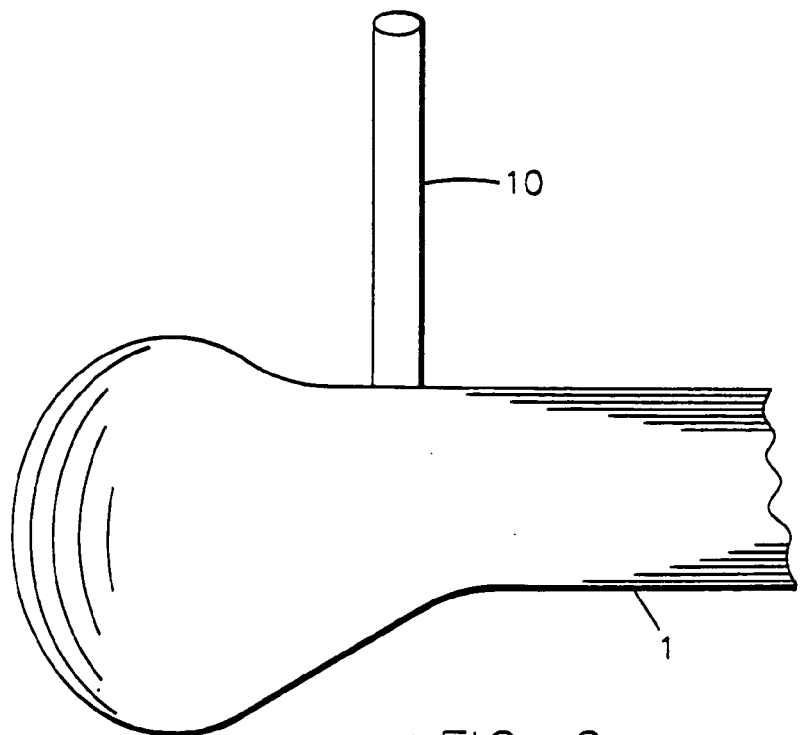
FIG. 2 is a side elevational view of the anchoring device installed in the distal femur.

Turning now to the Figures, the apparatus of the invention will be best understood by a description of the methods of the invention with reference to the Figures. As shown in FIGS. 1 and 2 an anchoring device 10 is installed in the bone 1 in a region proximal to the lateral anterior cortex and within the incision. The location for the anchoring device may be chosen by eye or with the aid of the tracking/navigation software, with an emphasis on paralleling the anchoring device body to the sagital plane. As shown in the Figures, the anchoring device 10 is a pin which is screwed into the bone. Other anchoring devices such as plates could be used, however.

Figure 3:
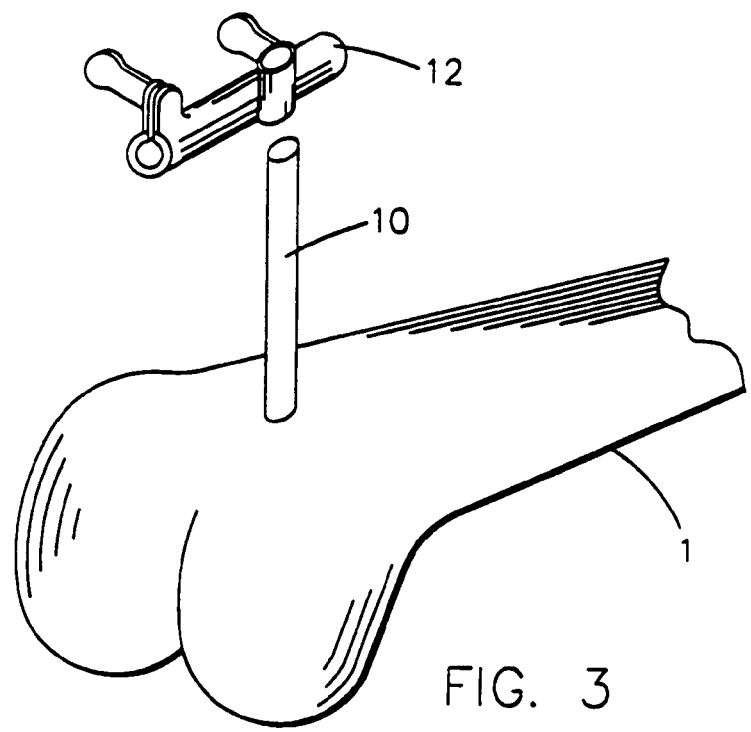
FIG. 3 is a perspective view of the anchoring device installed in the distal femur with a three-way alignment guide according to the invention not yet attached to the anchoring device.
Figure 4:
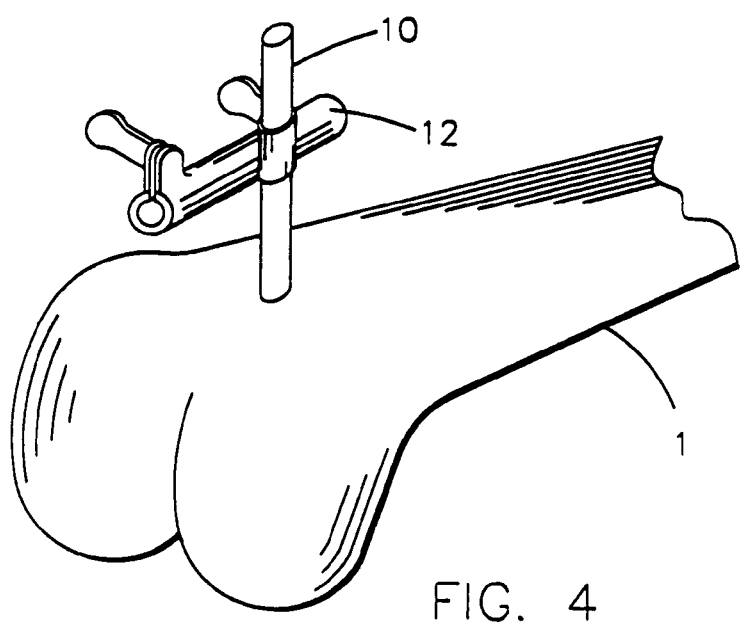
FIG. 4 is a view similar to FIG. 3 showing the alignment guide attached to the anchoring device.
Figure 5:
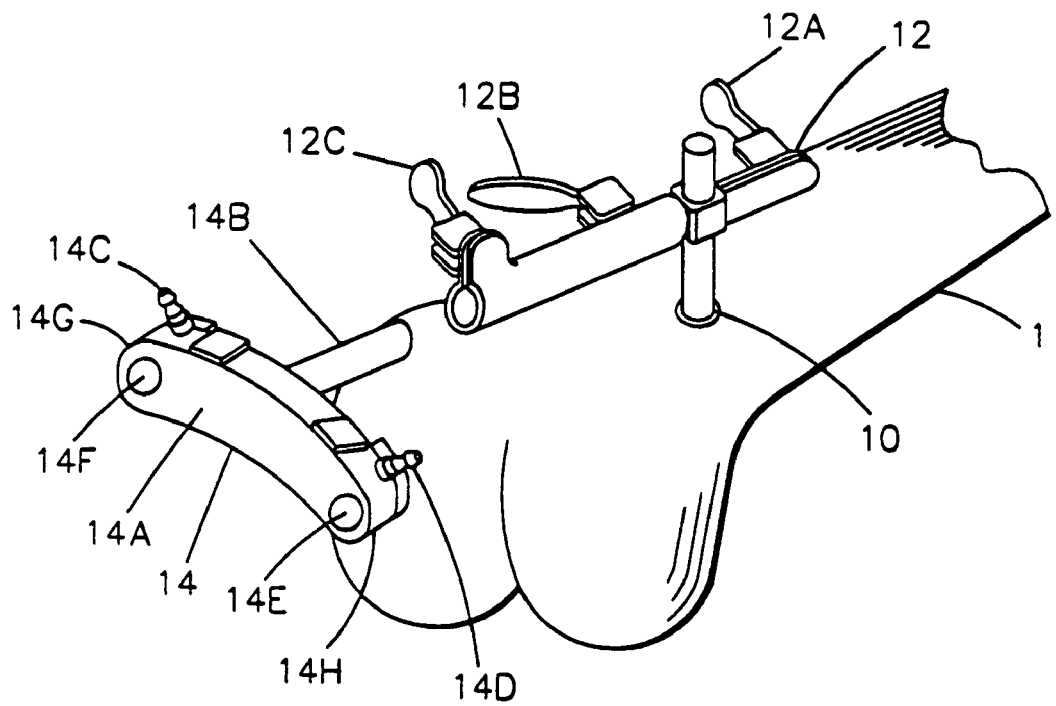
FIG. 5 is a perspective view showing a first embodiment of a resection guide according to the invention not yet attached to the three-way alignment guide.

With the anchoring device 10 in place, the alignment guide 12 is lowered on to it as shown in FIGS. 3-5. As seen best in FIG. 5, the alignment guide 12 has three cam locks 12a, 12b, 12c. The cam lock 12a allows the alignment guide to be adjusted according to flexion-extension angle relative to the anchoring device 10. The cam lock 12b allows the alignment guide to be adjusted according to varus-valgus angle relative to the anchoring device 10. The cam lock 12c opens the end of the alignment device to receive the resection guide 14 shown in FIGS. 5-7 and also allows for distal-proximal adjustment.

Figure 6:
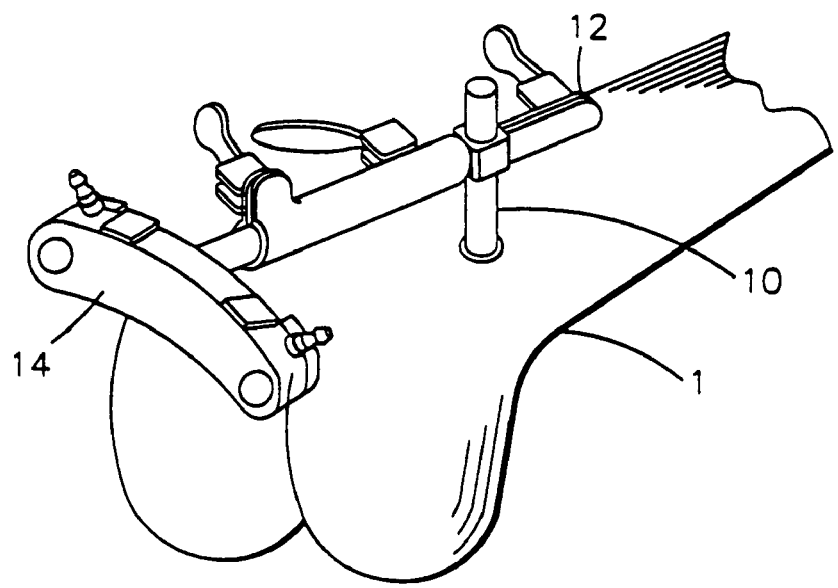
FIG. 6 is a perspective view showing a first embodiment of a resection guide according to the invention attached to the three-way alignment guide.
Figure 7:
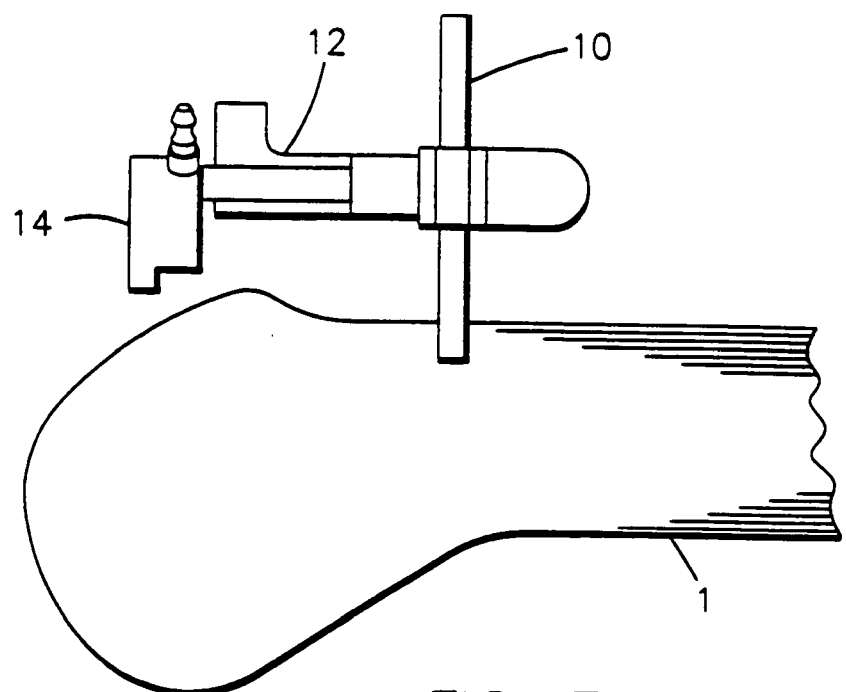
FIG. 7 is a side elevational view showing a first embodiment of a resection guide according to the invention attached to the three-way alignment guide.
Figure 10:
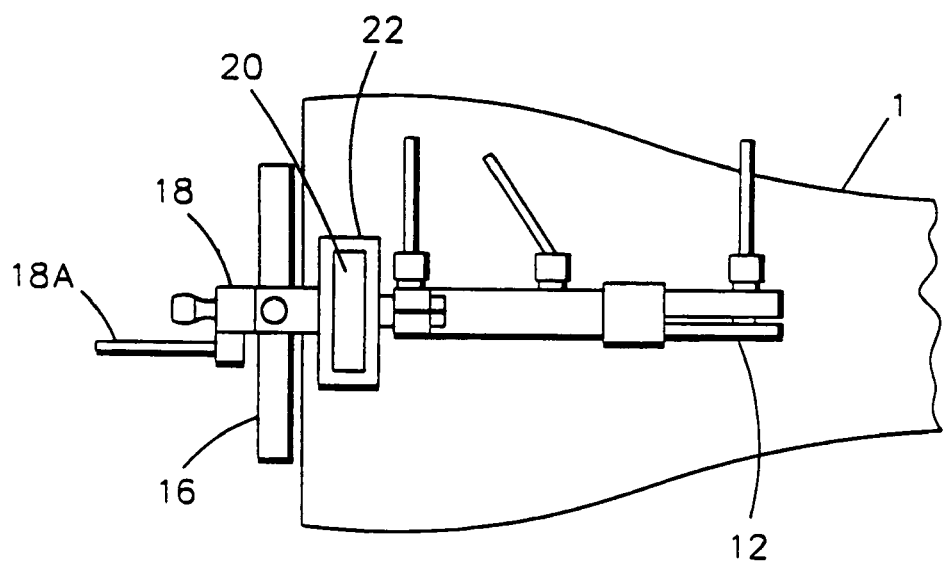
FIG. 10 is a plan view of the distal-proximal medial-lateral positioning guide, medial-lateral cam lock, anterior-posterior positioning guide, and femoral sizing block bushing coupled to the alignment guide.

Referring now to FIGS. 5-7, the resection guide 14 has a cutting guide surface 14a, an attachment rod 14b, a pair of connectors 14c, 14d for connecting trackers (not shown), a pair of rotatable pin guides 14e, 14f, and a pair of fail safe mounting bores 14g, 14h. The resection guide 14 is attached to the alignment guide 12 by opening cam lock 12c and inserting the attachment rod 14b into the alignment guide. It will be appreciated that the cam lock 12c allows proximal-distal positioning of the resection guide 14. After the resection guide 14 is attached to the alignment device 12, a tracker is attached to the guide 14.

With the tracker attached, the first cam lock 12a is opened and the resection guide is moved in the varus-valgus plane until the navigation software indicates the proper alignment. The cam lock 12a is then locked. Cam lock 12b is unlocked and the resection guide is moved in the flexion-extension plane until the navigation software indicates the proper alignment. The cam lock 12b is then locked.

Lastly, the cam lock 12c is opened and the resection guide is positioned in the proximal-distal plane until the navigation software indicates the proper alignment. The cam lock 12c is then locked. With the resection guide properly located, it may be affixed to the bone with pins (not shown) via the rotatable pin guides 14e, 14f. The pin guides are rotatable so that the practitioner may choose the best site for inserting a pin. The next step in the procedure is to resect the distal end of the femur using the resection guide 14.

Those skilled in the art will appreciate that if the anchor pin 10 is not substantially parallel to the sagital plane, the steps may need to be repeated to tune out error introduced by the misaligned anchor pin. One possible solution is to install the pin with a drill having an attached tracker thereby allowing the navigation software to guide the placement of the pin.

Following distal femoral resection, the femur is sized using either of the following methods:

1) Conventional sizing using either the Monogram or X-celerate sizing guides is performed. Surface digitization of the posterior condyles must be performed by the surgeon using the pointer by running the pointer tip over the posterior condylar bone and/or cartilage. The sizing guide is placed flush on the resected distal femur with the posterior skids against the posterior condyles. Either the sizing stylus or blade runner (or saw blade) is used to measure the most prominent aspect of the femoral lateral cortex. The femoral sizing block bushing can now be navigated.

Figure 8:
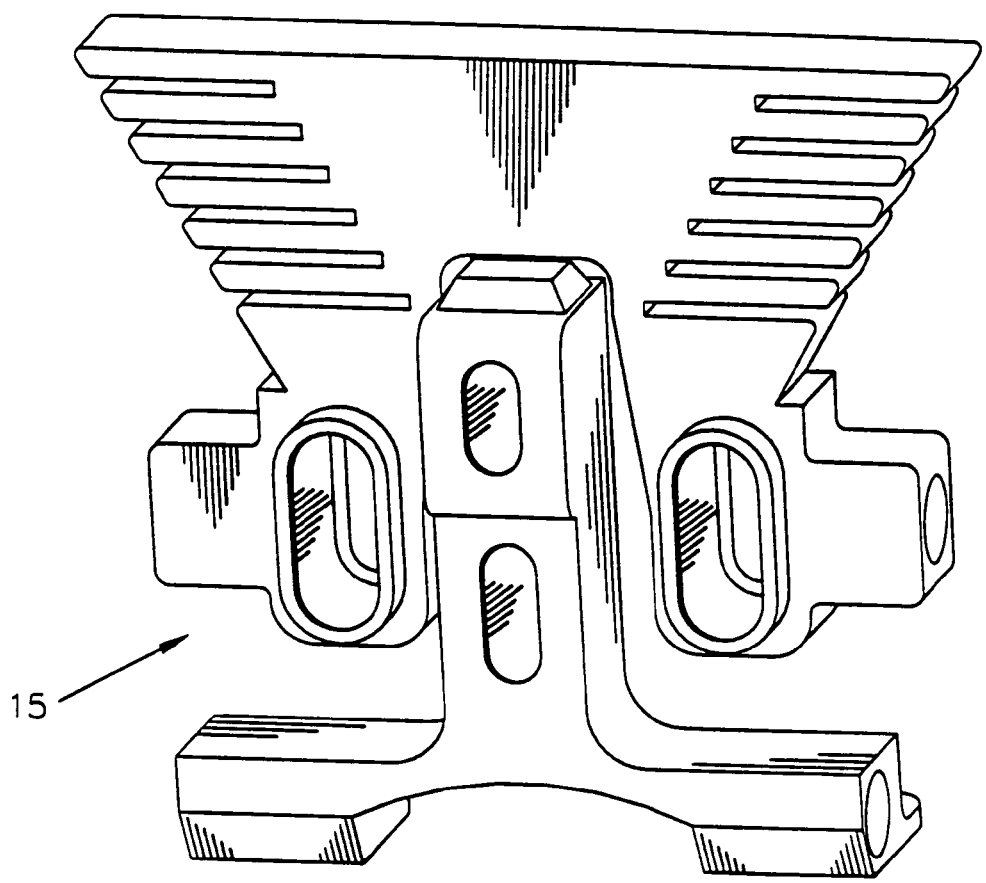
FIGS. 8 and 8A are perspective views of an anterior-posterior sizer.
Figure 8A:
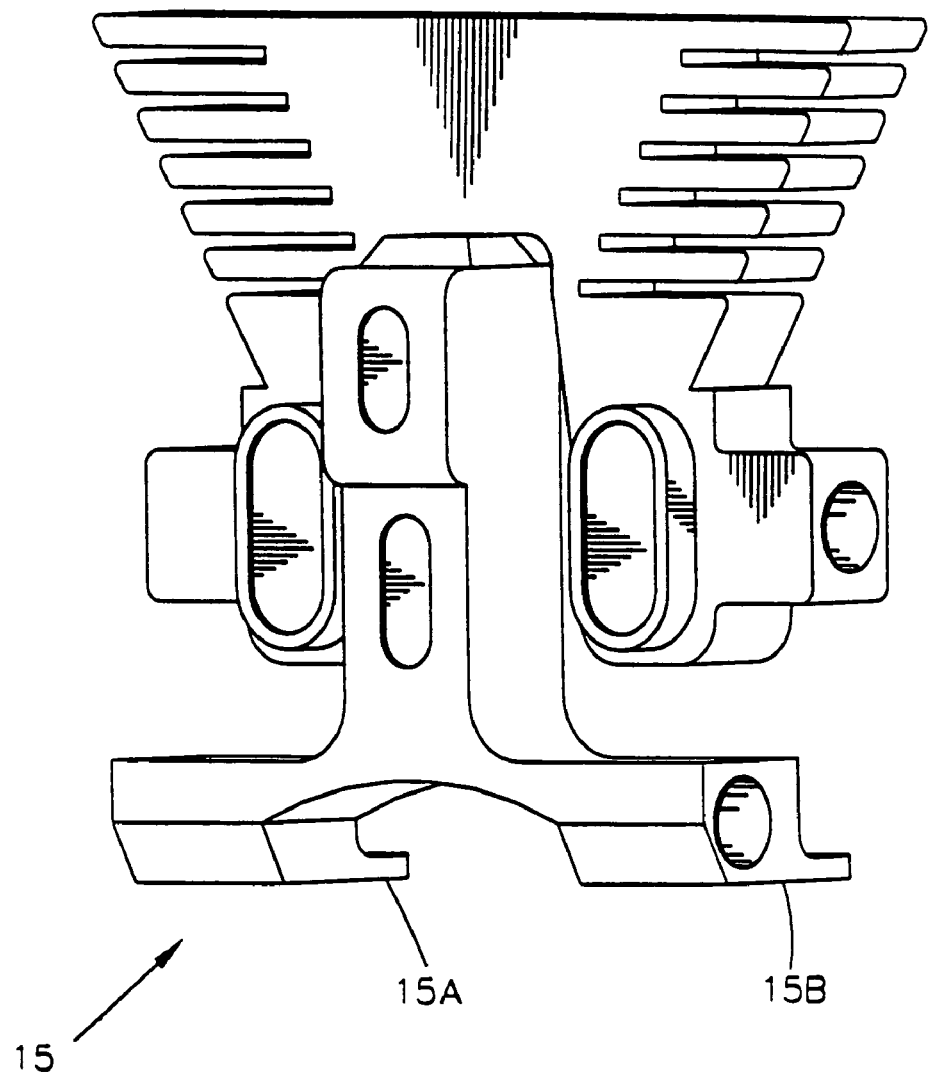
Figure 9:
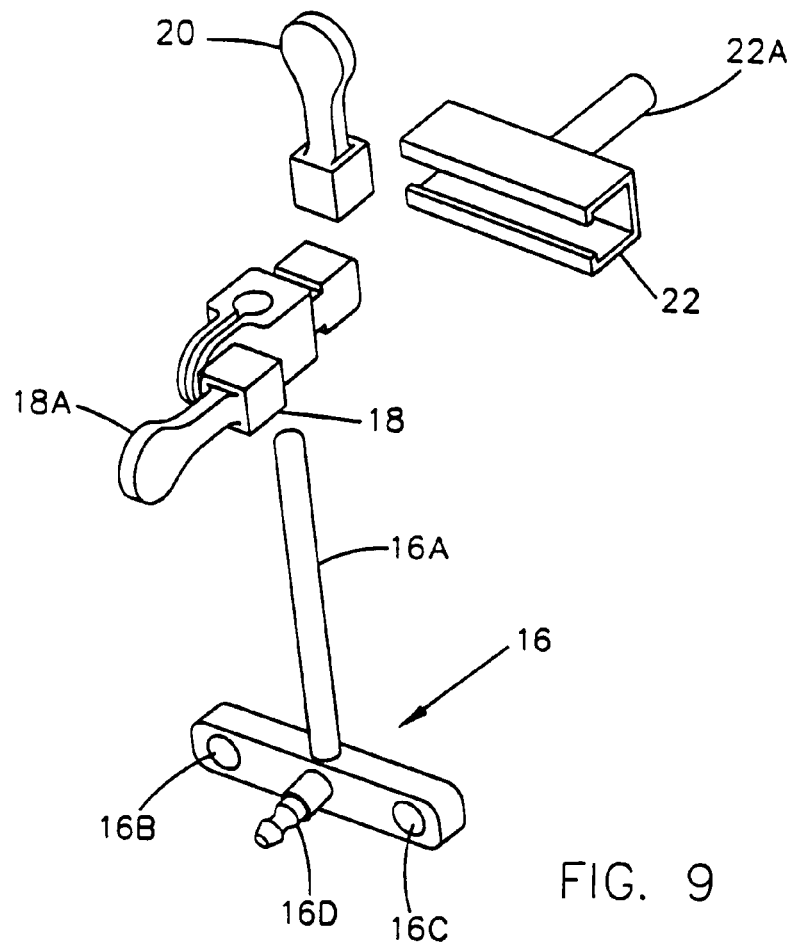
FIG. 9 is an exploded perspective view of the distal-proximal medial-lateral positioning guide, medial-lateral cam lock, anterior-posterior positioning guide, and femoral sizing block bushing.
Figure 13:
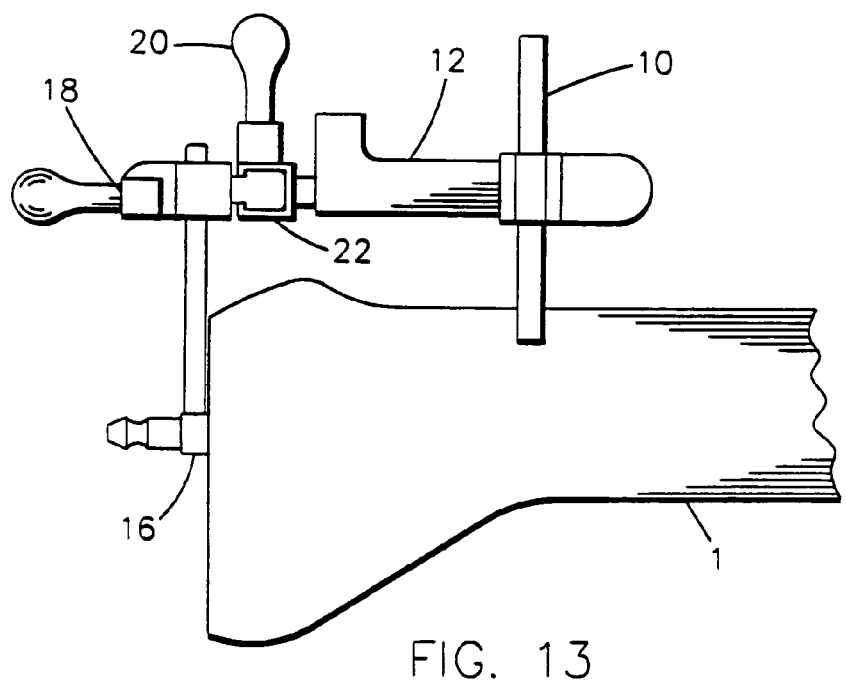
FIG. 13 is a side elevation view of the distal-proximal medial-lateral positioning guide, medial-lateral cam lock, anterior-posterior positioning guide, and femoral sizing block bushing coupled to the alignment guide.
Figure 11:
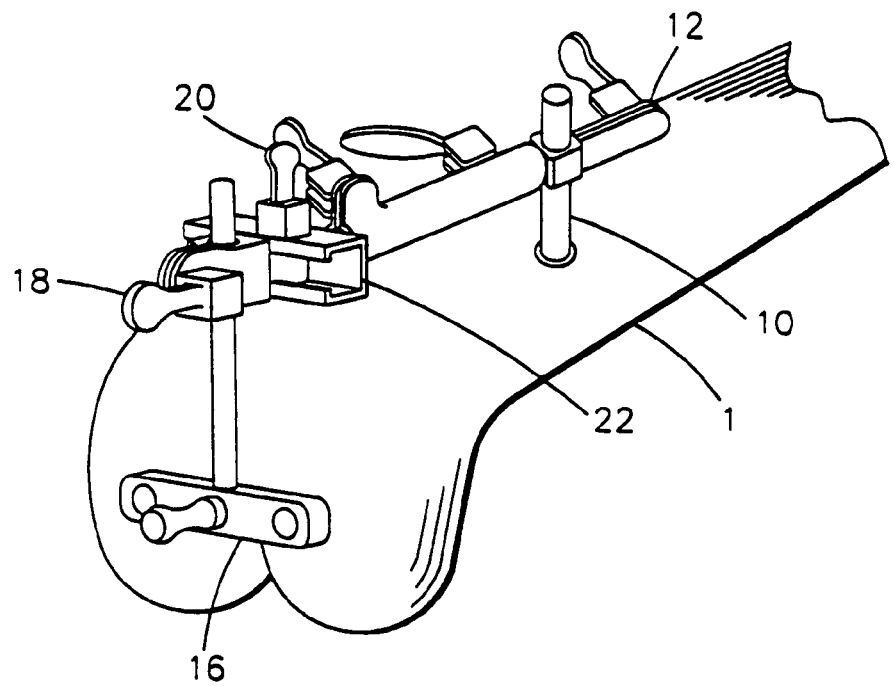
FIGS. 11 and 12 are perspective views of the distal-proximal medial-lateral positioning guide, medial-lateral cam lock, anterior-posterior positioning guide, and femoral sizing block bushing coupled to the alignment guide.
Figure 12:
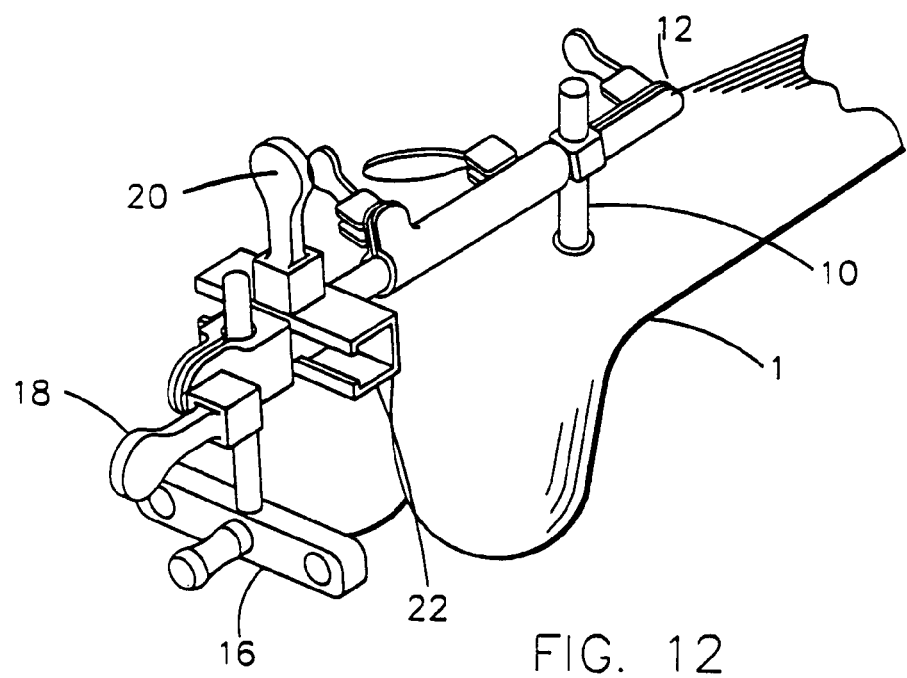

An exemplary sizing guide 15 is shown in FIGS. 8 and 8a. The adjustable A-P sizer 15 sets internal-external rotation and also allows an AP movement of +/−2 mm. This instrument is used after the femoral distal cut is performed. The feet 15a, 15b are inserted under the posterior condyles. The jig is allowed to move through six degrees either internally or externally as shown by the indicia between the letters "L" and "R".

A blade runner is introduced into one of the slots (labeled in 3, 5, 7, 9, 11, and 13 mm). The slot selected is the one that gives the required run-out anteriorly. If the surgeon is in between sizes, if he goes down a size, he will notch the femur, or if he moves up a size he will leave a gap. The jig allows the surgeon to obtain the optimal position.

2) Alternatively, software algorithms are used to size the femur. Surface digitization of the trochlear groove (patella track) and posterior condyles are performed by the surgeon using the pointer by running the pointer tip over the posterior condylar bone and/or cartilage. Digitized data is analyzed in the sagital plane. Direct correlation to (or matching of) the correct femoral component is achieved via the software coding/algorithms. The surgeon will be able to visualize the matching on the operating room computer monitor (graphical interface). Sizing is complete using solely digitization methods. The femoral sizing block bushing can now be navigated.

Turning now to FIGS. 9-13, after the distal femur is resected and sizing is completed, the appropriately sized femoral sizing block bushing 16 is attached to the alignment guide 12 using an anterior-posterior positioning guide 18 having a cam lock 18a, a medial-lateral cam lock 20, and a distal-proximal medial-lateral positioning guide 22. The bushing 16 has a vertical shaft 16a, a pair of drill guides 16b, 16c, and a tracker coupling 16d. The vertical shaft 16a is inserted into the anterior-posterior positioning guide 18 which is coupled to the medial-lateral cam lock 20 which is slidably coupled to the distal-proximal medial-lateral positioning guide 22.

A tracker (not shown) is coupled to the coupling 16d. Using the cam locks, the distal-proximal position is set by manually presenting the bushing 16 to the resected face of the femur. The internal-external rotation is navigated and the cam lock is locked on the positioning guide. The medial-lateral positioning of the bushing is navigated and locked using the medial-lateral cam lock 20. Finally, anterior-posterior positioning is navigated and locked with the cam lock 18a. Verification of the navigated position is done in conjunction with the screens on the computer. Once satisfied with the navigated position, two holes are drilled through the drill guides 16b, 16c. The complete anchoring mechanism is removed and the appropriate femoral cutting block is attached.

Figure 14:
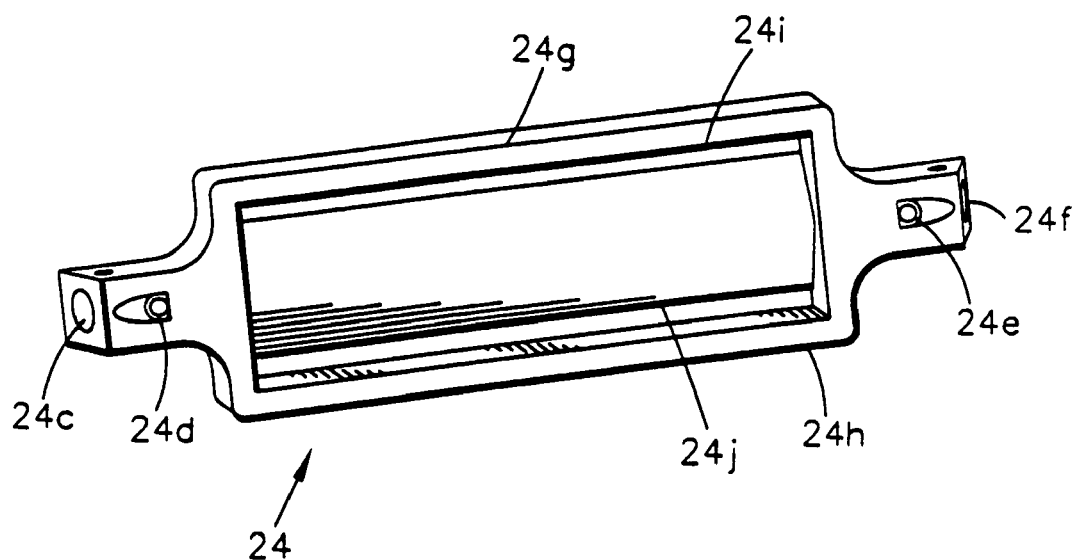
FIGS. 14 and 15 are perspective views of a femoral cutting guide.
Figure 15:
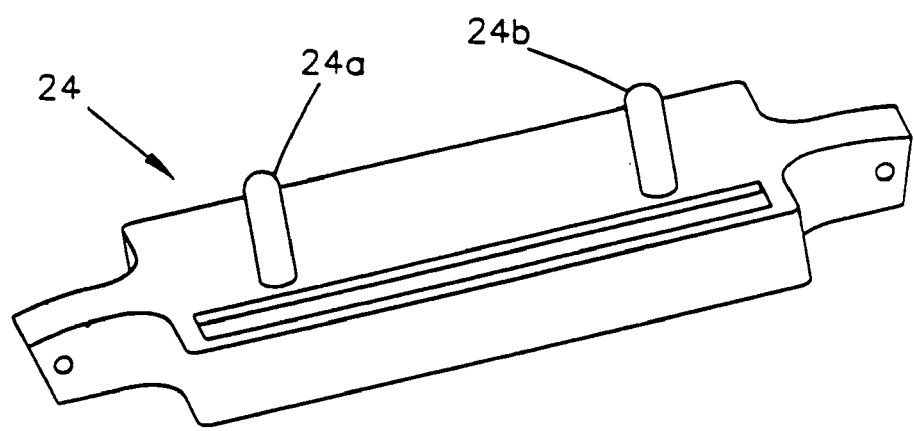
Figure 16:
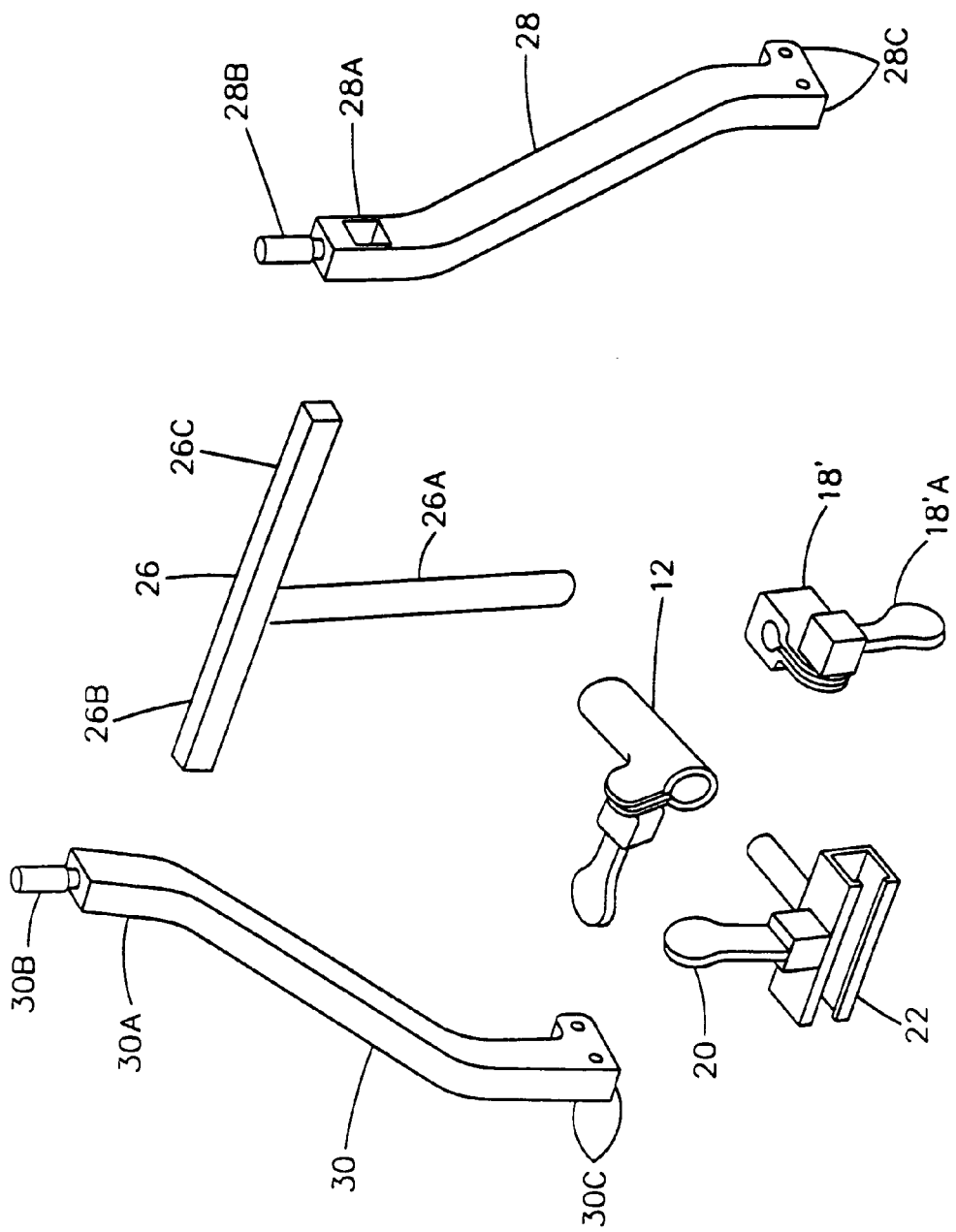
FIG. 16 is an exploded perspective view of a pivotal 5-in-1 positional alignment jig and five-way alignment guide.

FIGS. 14 and 15 illustrate an exemplary cutting block 24. The cutting block 24 has a pair of pins 24a, 24b which are impacted into the holes drilled with the bushing 16 (described above).

Additional fixation holes 24c-24f are provided for optional fixation with pins. The cutting guide has four guiding surfaces: the anterior cut guiding surface 24g, the posterior cut guiding surface 24h, the anterior chamfer cut guiding surface 24i, and the posterior chamfer cut guiding surface 24j. After these four cuts are made, the cutting block is removed and the femur is near ready for accepting the prosthesis.

A second embodiment of the methods and tools of the invention is illustrated with reference to FIGS. 16 through 21. The second embodiment utilized the same anchoring device 10, alignment guide 12, and the alignment devices 18, 20, 22 with a minor alteration. The anterior-posterior alignment device 18' shown in the Figures has its cam lock 18'a oriented in a slightly different position than the cam lock 18a on the alignment device 18. According to this embodiment, the devices 12, 18', 20, and 22 are assembled to provide what amounts to a six-way alignment guide. Further according to this embodiment, a pivotal 5-in-1 positional alignment jig is provided which includes the components 26, 28, and 30. Component 26 is a T-bar having a vertical shaft 26a, a lateral arm 26b and a medial arm 26c. Component 28 is a medial drilling guide arm having a mounting hole 28a, a set screw 28b, and drill guides 28c. Component 30 is a lateral drilling guide arm having a mounting hole 30a, a set screw 30b, and drill guides 30c.

Figure 17:
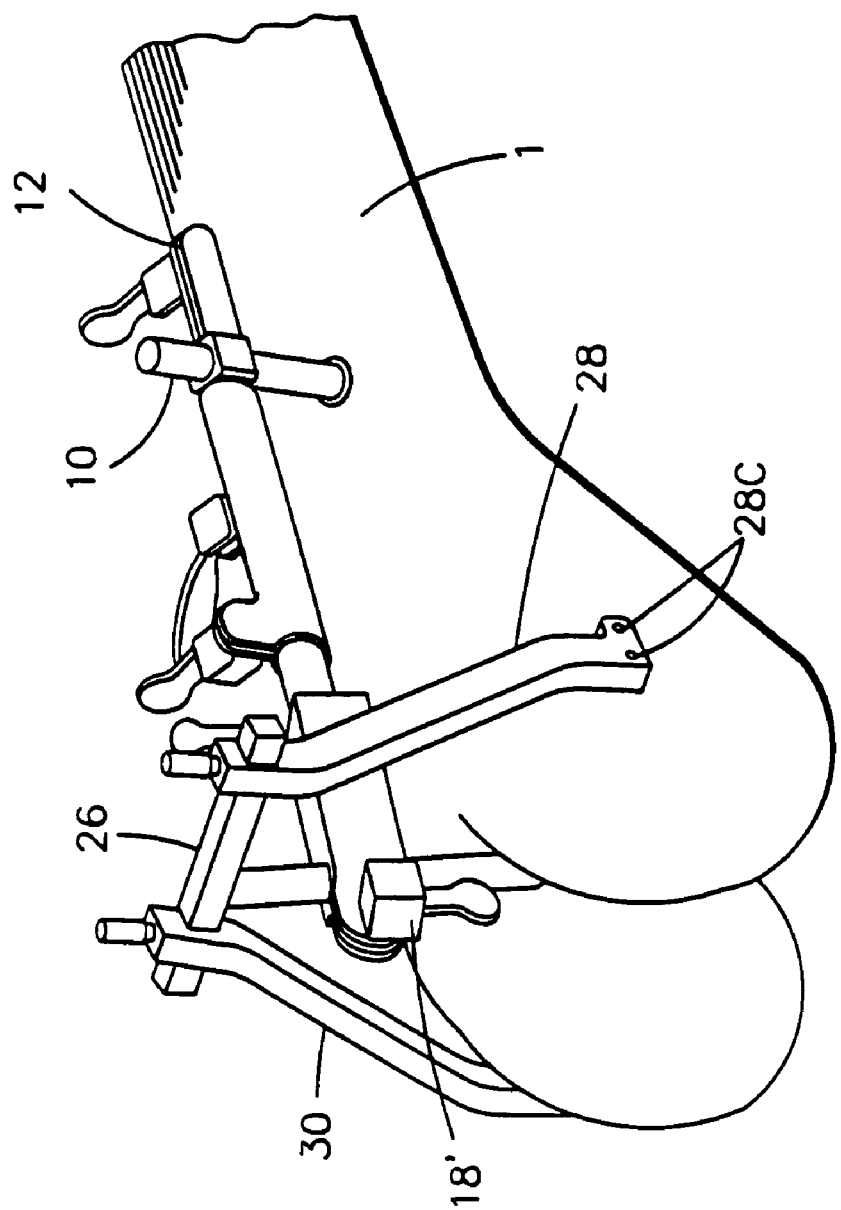
FIGS. 17-19 are perspective views of the pivotal 5-in-1 positional alignment jig and five-way alignment guide coupled to the anchoring device.
Figure 18:
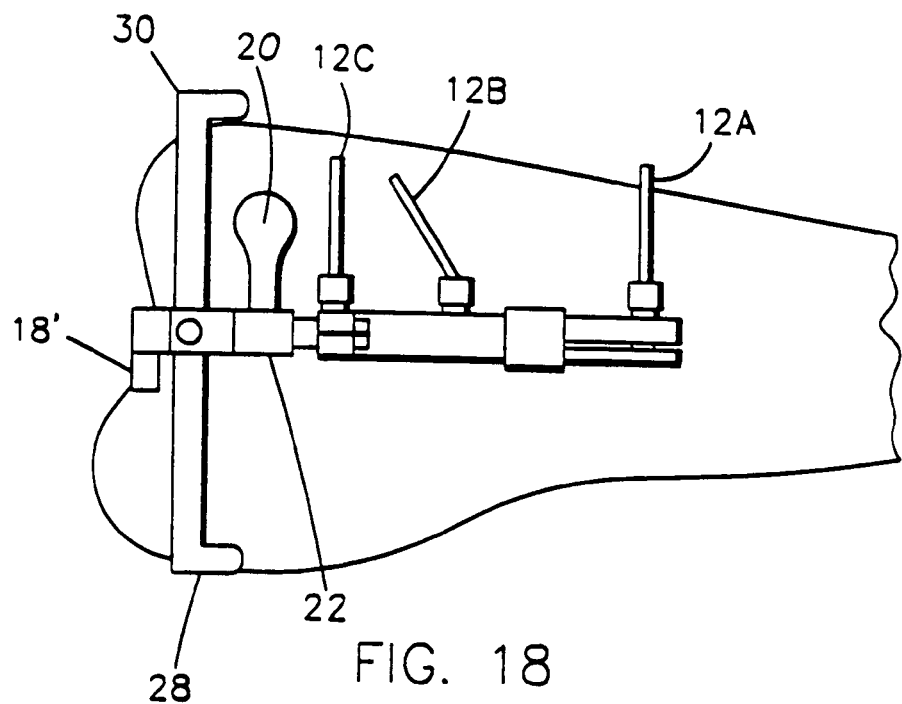
Figure 19:
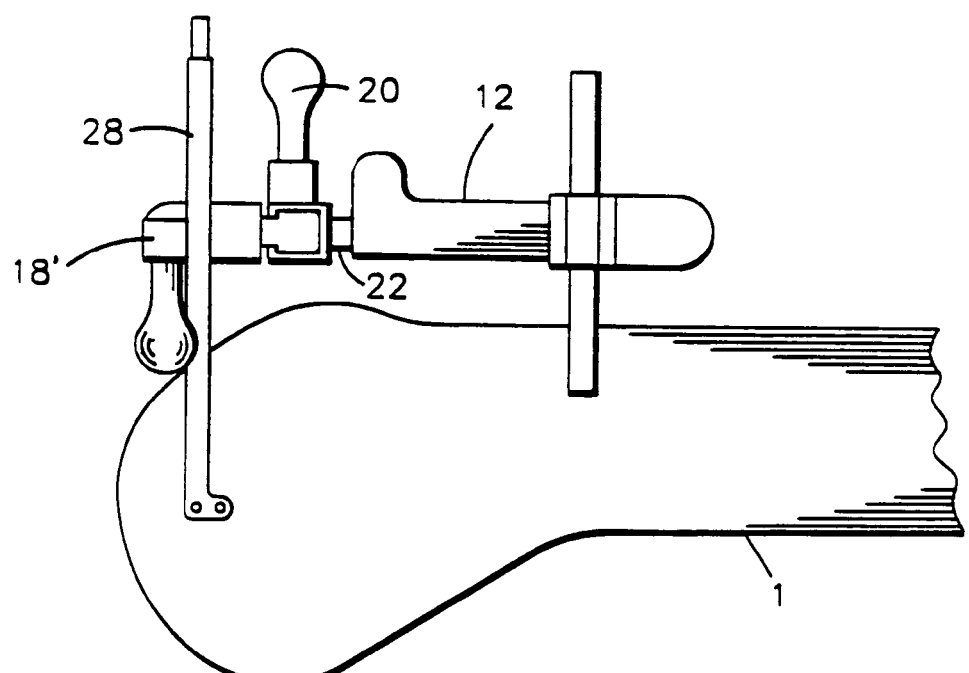

After the femur is digitized as described above with reference to the first embodiment, the components are assembled as shown in FIGS. 17-19. A tracker (not shown) is attached to one of the set screws 28b, 30b.

Using the various CAM locks, the medial and lateral drilling guides 28, 30 are positioned in the following directions in the following order: varus-valgus, flexion-extension, internal-external rotation, distal-proximal, and anterior-posterior directions.

More particularly, the sequential locking of the guide begins with flexion-extension. The cam lock 12b is opened and the jig is navigated until the recommended position is reached. Once reached, the flexion-extension cam lock 12b is engaged.

Next, varus-valgus lock 12a is opened and flexion-extension is navigated. The jig is navigated until the recommended position is reached. Once attained, the varus-valgus cam lock 12a is engaged. Next, internal-external rotation is navigated. The cam lock 12c is opened and the jig is navigated until the recommended positions are reached.

Once attained, the internal-external rotation and distal-proximal translation are engaged. Next, anterior-posterior positioning is navigated. The cam lock 18a is opened and the jig is navigated until the recommended position is reached. Once attained, the anterior-posterior cam lock 18a is engaged. The medial-lateral positioning is not performed until the 5-in-1 cutting guide is attached as described below with reference to FIG. 21.

After the drilling guides are positioned, four holes are drilled into the epicondylar region using the drill guides 28c, 30c. All of the devices are then removed from the femur.

Figure 20:
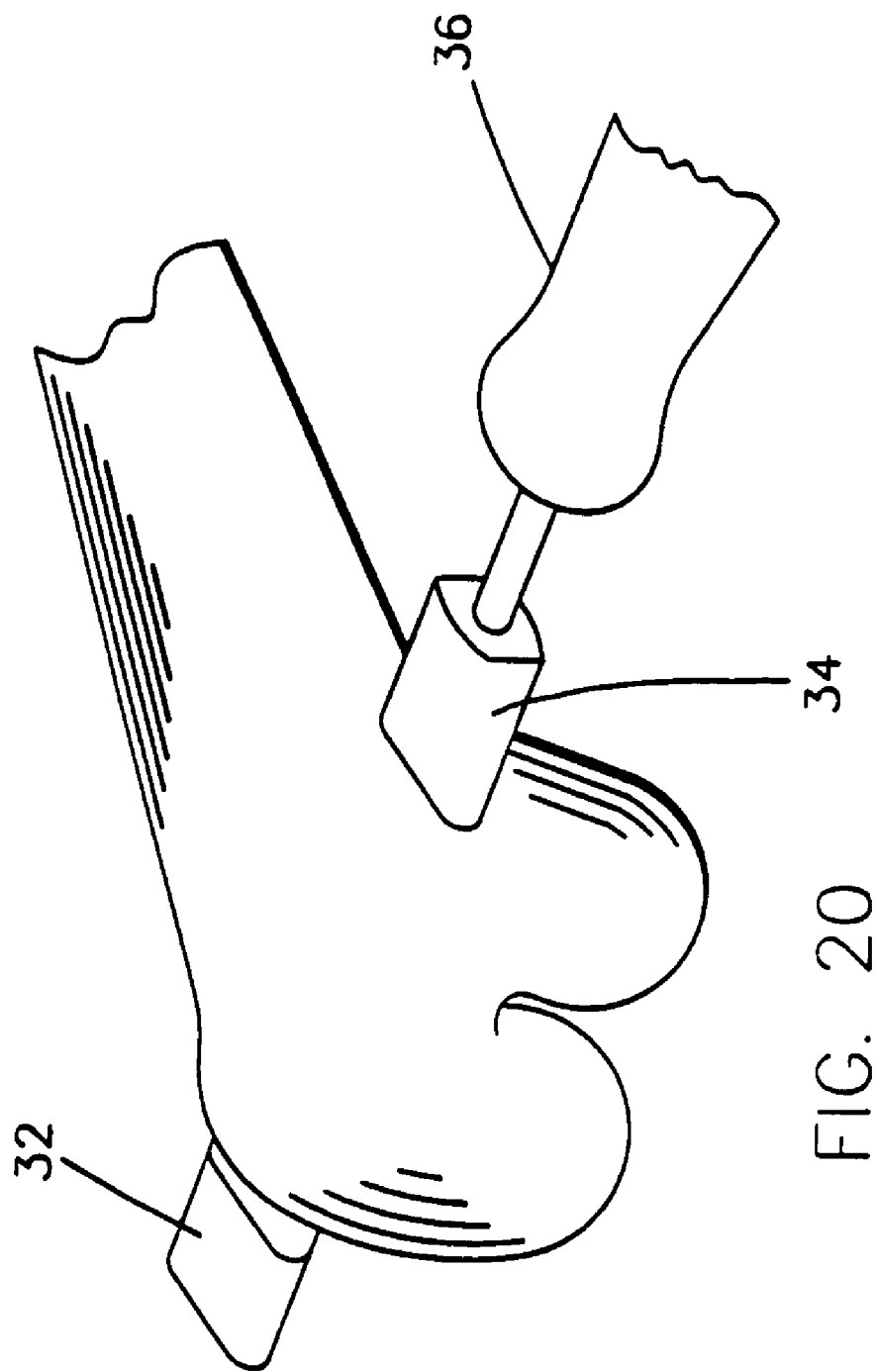
FIG. 20 is a perspective view of a pair of diodes coupled to the epicondylar region of the femur.

Referring now to FIG. 20, a pair of diodes 32, 34 are installed in the epicondylar region with screws (not shown), in the holes which were drilled in the previous step, using a screwdriver 36.

Figure 21:
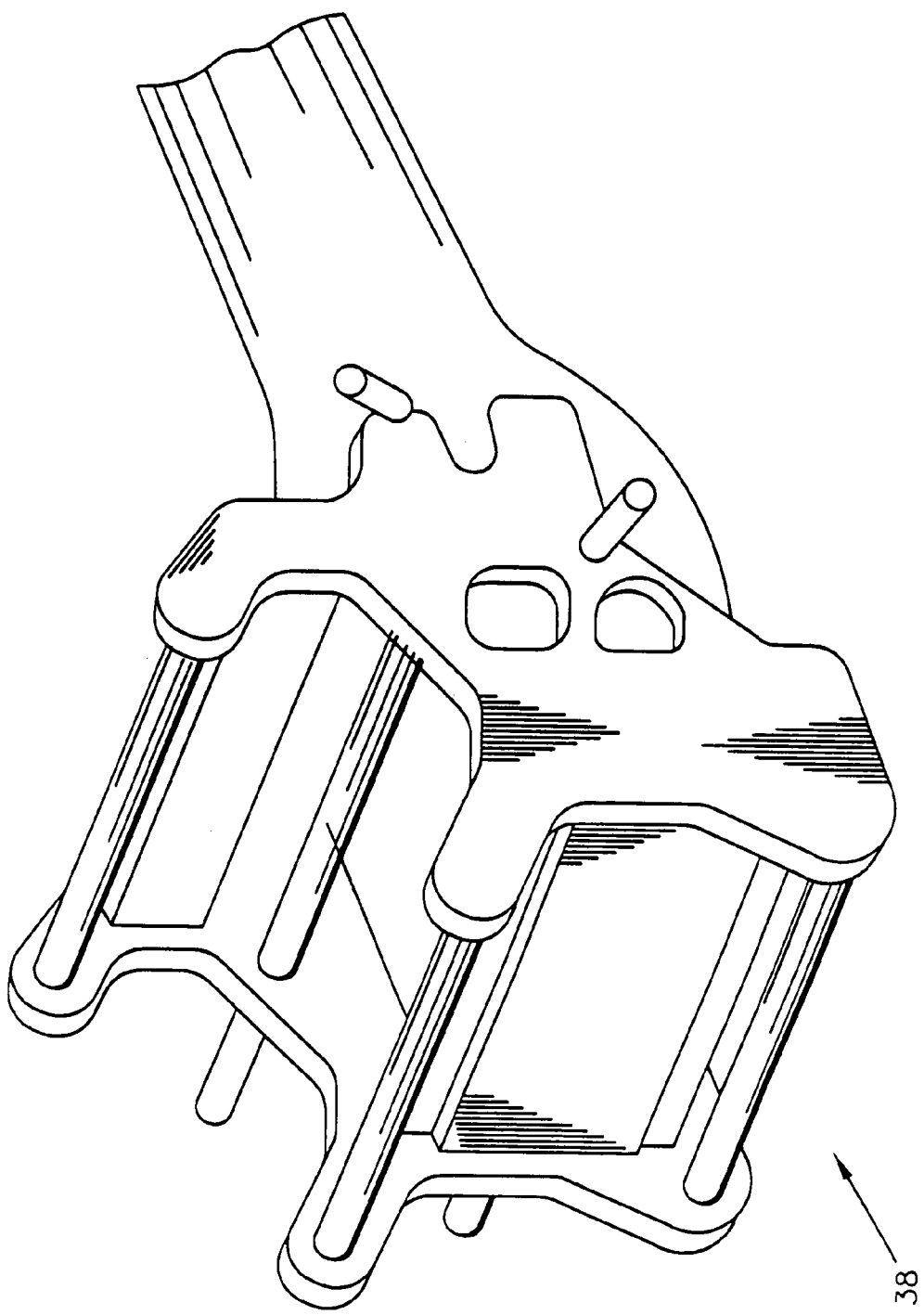
FIG. 21 is a perspective view of a 5-in-one cutting block mounted on the diodes.

Turning now to FIG. 21, a 5-in-1 cutting guide 38 is mounted on the diodes as described in previously incorporated application Ser. No. 09/746,800. Prior to fixing the cutting guide with pins, the medial-lateral position of the guide is fine tuned by the surgeon. The 5-in-1 cutting block is then pinned in position and is used to perform all of the femoral cuts as described in previously incorporated application Ser. No. 09/746,800.

There have been described and illustrated herein methods and tools for resection of the distal femur. While particular embodiments of the invention have been described, it is not intended that the invention be limited thereto, as it is intended that the invention be as broad in scope as the art will allow and that the specification be read likewise. For example, the first two positioning steps may be reversed in sequence, provided that the navigation software is suitable modified. Moreover, the clamps on the alignment guides need not be cam locks, but could be other types of clamps. Although the apparatus has been described as separate pieces (e.g. the anchor, the alignment guide, and the resection guide), it could be two pieces or a single piece. In general, the methods and tools of the invention could be used with other joints other than the knee. It is believed that the methods and tools could be used in arthroplasty of the hip, shoulder, elbow, etc.

What is claimed is:

1. An apparatus for use during arthroplasty for guiding the resection of a bone having a long axis, comprising:
   an anchoring pin for anchoring the apparatus to the bone, said anchoring pin oriented transversely to the long axis of the bone;
   a first cam lock having a rod member at a first end and a split bore at a second end for slidably and rotationally receiving the pin, a diameter of the split bore being reduced by actuation of a first cam lever forming part of the first cam lock;
   a first split tubular member having a bore with a first longitudinal axis, a second cam lock located at a first end of the first split tubular member, the rod member slidably and rotationally received within the bore at a first end of the first split tubular member, a diameter of the first split tubular member bore reduced by the actuation of a second cam lever forming part of the second cam lock;
   a third cam lock located at the second end of the first split tubular member, a diameter of the first split tubular member bore at a second end thereof reduced by the actuation of a third cam lever forming part of the third cam lock, a positioning guide having a rod thereon mounted in the second end of the first split tubular member and locked in the bore by the third cam lock, the positioning guide having a track thereon extending in a plane perpendicular to the longitudinal axis of the first split tubular member bore, the track having a fourth cam lock, the track slidably receiving an element having a fifth cam lock having a second split tubular member having a bore capable of being reduced by actuation of a fifth cam lever, the element having the fifth cam lock is slidable on the track along a plane perpendicular to the longitudinal axis of the first split tubular member and capable of being locked in the track by the fourth cam lock, a guide having a rod slidably mounted in the second split tubular member bore and capable of being locked in the bore of the fifth cam lock by the fifth cam lever, the guide slidable in a plane parallel to the plane of the track and perpendicular to the first longitudinal axis of the split tubular member, the second direction perpendicular to the first direction, said apparatus providing six degrees of freedom, wherein said six degrees of freedom include three rotations and three orthogonal translations.

2. The apparatus according to claim 1 wherein said six degrees of freedom include flexion-extension, varus-valgus, and proximal-distal.

3. The apparatus according to claim 2 wherein said six degrees of freedom include flexion-extension, varus-valgus, internal-external rotation, proximal-distal, medial-lateral, and anterior-posterior.

4. The apparatus according to claim 1 wherein said guide includes means for attaching a computer navigation tracker.

5. The apparatus according to claim 1 wherein said guide includes a pair of arms having guide holes adapted to guide drilling into the epicondylar region of a femur.

6. The apparatus according to claim 5 wherein said guide includes a T-shaped component and said arms are adapted to be coupled to said T-shaped component.

7. The apparatus according to claim 1 wherein said guide is adapted to guide the drilling of two holes in the distal femur.

8. The apparatus of claim 1 wherein said anchoring means is oriented substantially parallel to the sagital plane.

9. A set of tools for guiding the resection of a bone during arthroplasty, said set of tools comprising:
   a guide bushing defining two spaced apart guide holes, said guide bushing having an orthogonal stem for coupling to an alignment device and a coupling for coupling a tracker to the bushing, the guide bushing moveable in a direction with respect to the stem transverse to a longitudinal axis of the stem;
   an alignment device having six degrees of freedom wherein three are rotational and three are orthogonal translations, said alignment device being adapted to couple to said stem and couple to an anchoring device;
   the alignment device comprising:
   a first cam lock having a rod member at a first end and a split bore at a second end for slidably and rotationally receiving the anchoring device coupled to a bone, a diameter of the split bore being reduced by actuation of a first cam lever forming part of the first cam lock;
   a first split tubular member having a bore with a first longitudinal axis, a second cam lock located at a first end of the first split tubular member, the rod member slidably and rotationally received within the bore at a first end of the first split tubular member, a diameter of the first split tubular member bore reduced by the actuation of a second cam lever forming part of the second cam lock;
   the guide bushing orthogonal stem slidably and rotationally received within a bore at a second end of the first split tubular member; and
   a third cam lock located at the second end of the first split tubular member, a diameter of the first split tubular member bore at the second end reduced by the actuation of a third cam lever forming part of the third cam lock, the guide bushing having a rod thereon mounted in the second end of the first split tubular member and locked in the bore by the third cam lock, the positioning guide having a track thereon extending in a plane perpendicular to the longitudinal axis of the first split tubular member bore, the track having a fourth cam lock, the track slidably receiving an element having a fifth cam lock having a second split tubular member having a bore capable of being reduced by actuation of a fifth cam lever, the element having the fifth cam lock is slidable on the track along a plane perpendicular to the longitudinal axis of the first split tubular member bore and capable of being locked in the track by the fourth cam lock, a guide having a rod slidably mounted in the second split tubular member bore and capable of being locked in the bore of the fifth cam lock by the fifth cam lever, the guide slidable in a plane parallel to the plane of the track and perpendicular to the first longitudinal axis of the split tubular member, the second direction perpendicular to the first direction.

10. The set of tools according to claim 9 wherein said guide is adapted to guide the drilling of holes in the distal femur.

11. The set of tools according to claim 9 wherein said alignment device has six degrees of freedom.

12. The set of tools according to claim 9 wherein said guide bushing includes a medial guide hole and a lateral guide hole, said medial guide hole for drilling into the medial condylar region, and said lateral guide bushing for drilling into the lateral condylar region.

13. A set of tools for guiding the resection of a bone during arthroplasty, said set of tools comprising:
   a resection guide comprising a guide bushing having an orthogonal stem for coupling to an alignment device and a coupling for coupling a tracker to the guide;
   an alignment device for aligning the resection guide having three rotational degrees of freedom and three orthogonal translational degrees of freedom comprising:
   a first cam lock having a rod member at a first end and a split bore at a second end for slidably and rotationally receiving a pin extending into a bone, a diameter of the split bore being reduced by actuation of a first cam lever forming part of the first cam lock;
   a first split tubular member having a bore with a first longitudinal axis, a second cam lock located at a first end of the first split tubular member, the rod member slidably and rotationally received within the bore at a first end of the first split tubular member, a diameter of the first split tubular member bore reduced by the actuation of a second cam lever forming part of the second cam lock;
   the guide bushing orthogonal stem slidably and rotationally received within a bore at a second end of the first split tubular member, the guide bushing movable in a direction with respect to the stem transverse to a longitudinal axis of the stem; and
   a third cam lock located at the second end of the first split tubular member, a diameter of the split tubular member bore at the second end reduced by the actuation of a third cam lever forming part of the third cam lock, the guide bushing having a positioning guide having a rod thereon mounted in the second end of the first split tubular member and locked in the bore by the third cam lock, the positioning guide having a track thereon extending in a plane perpendicular to the longitudinal axis of the first split tubular member bore, the track having a fourth cam lock, the track slidably receiving an element having a fifth cam lock having a second split tubular member having a bore capable of being reduced by actuation of a fifth cam lever, the element having the fifth cam lock is slidable on the track along a plane perpendicular to the first longitudinal axis of the first split tubular member and capable of being locked in the track by the fourth cam lock, a guide having a rod slidably mounted in the second split tubular member bore and capable of being locked in the bore of the fifth cam lock by the fifth cam lever, the guide slidable in a plane parallel to the plane of the track and perpendicular to the first longitudinal axis of the split tubular member, the second direction perpendicular to the first direction.

14. The set of tools according to claim 13 wherein said guide is adapted to guide the drilling of holes in the distal femur.

15. The set of tools according to claim 13 wherein said guide is a guide bushing which includes a medial guide hole and a lateral guide hole, said medial guide bushing hole for drilling into the medial condylar region, and said lateral guide bushing hole for drilling into the lateral condylar region.

* * * * *